US010853452B1

(12) United States Patent
Ahern et al.

(10) Patent No.: US 10,853,452 B1
(45) Date of Patent: Dec. 1, 2020

(54) INCENTIVE BASED DISCOUNT SYSTEM

(71) Applicant: Abacus Health Solutions, Cranston, RI (US)

(72) Inventors: David K. Ahern, Tiverton, RI (US); Michael J. Follick, Providence, RI (US); Edward Aberger, Cranston, RI (US); Linda Loiselle, Providence, RI (US); Joseph Wroblewski, Attleboro, MA (US); Augustus E. Adams, III, South Grafton, MA (US); Sean Follick, Providence, RI (US)

(73) Assignee: Abacus Health Solutions, Cranston, RI (US)

( * ) Notice: Subject to any disclaimer, the term of this patent is extended or adjusted under 35 U.S.C. 154(b) by 583 days.

(21) Appl. No.: 15/343,423

(22) Filed: Nov. 4, 2016

Related U.S. Application Data

(60) Provisional application No. 62/251,279, filed on Nov. 5, 2015.

(51) Int. Cl.
*G06Q 30/02* (2012.01)
*G06F 19/00* (2018.01)

(52) U.S. Cl.
CPC ....... *G06F 19/328* (2013.01); *G06Q 30/0207* (2013.01)

(58) Field of Classification Search
CPC .......................... G06F 19/328; G06Q 30/0207
See application file for complete search history.

(56) References Cited

U.S. PATENT DOCUMENTS

2005/0187790 A1* 8/2005 Lapsker .............. G06F 19/3456 705/2
2005/0187793 A1 8/2005 Myles
2005/0187821 A1 8/2005 Lapsker
2005/0240442 A1 10/2005 Lapsker
2006/0009684 A1* 1/2006 Kim ..................... A61B 5/0002 600/300
2006/0085231 A1 4/2006 Brofman
2006/0118436 A1 6/2006 Lapsker
2007/0233526 A1 10/2007 Hoffman et al.
2014/0164003 A1* 6/2014 Thesman ............... G06Q 50/22 705/2
2015/0278472 A1* 10/2015 King .................. G06F 19/3456 705/2

OTHER PUBLICATIONS

Ahern, et al., "eHeath for Employee Health and Wellness—Optimizing Plan Design and Incentive Management", Chapter 29:248-2558, 2009.

* cited by examiner

*Primary Examiner* — Michael Tomaszewski
*Assistant Examiner* — Mohmad Muqueeth
(74) *Attorney, Agent, or Firm* — Fish & Richardson P.C.

(57) ABSTRACT

Methods, systems, and apparatus, including computer programs encoded on computer storage media, for touchpoint management. One of the methods includes receiving compliance information about a member. The method includes determining based at least in part on the compliance information that the member is in compliance with the health plan. The method includes adding the member to a list of compliant members. The method also includes providing the list of compliant members to at least one third-party.

16 Claims, 5 Drawing Sheets

LAB
102
104
106
108
110

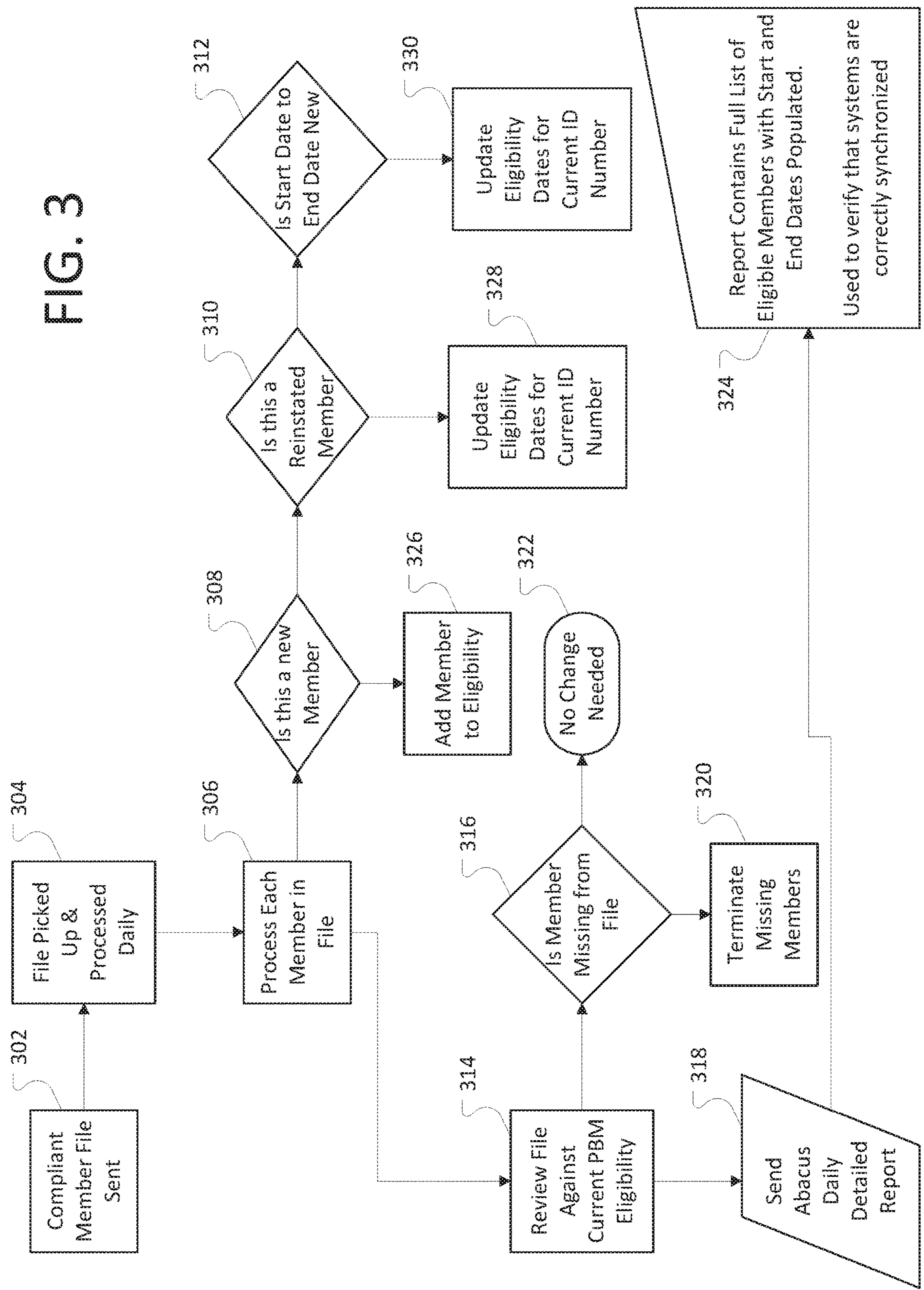
FIG. 3
Compliant Member File Sent
302
File Picked Up & Processed Daily
304
Process Each Member in File
306
Is this a new Member
308
Add Member to Eligibility
326
Is this a Reinstated Member
310
Update Eligibility Dates for Current ID Number
328
Is Start Date to End Date New
312
Update Eligibility Dates for Current ID Number
330
Review File Against Current PBM Eligibility
314
Is Member Missing from File
316
No Change Needed
322
Terminate Missing Members
320
Send Abacus Daily Detailed Report
318
Report Contains Full List of Eligible Members with Start and End Dates Populated.
Used to verify that systems are correctly synchronized
324

INCENTIVE BASED DISCOUNT SYSTEM

CLAIM OF PRIORITY

This application claims priority under 35 USC § 119(e) to U.S. Patent Application Ser. No. 62/251,279, filed on Nov. 5, 2015, and titled “INCENTIVE BASED DISCOUNT SYSTEM” the entire contents of which are hereby incorporated by reference.

BACKGROUND

A prescription is a written directive for the compounding or dispensing and administration of drugs or for other service to a particular patient.

Federal law divides medicines into two main classes: prescription medicines and over-the-counter medicines. Dangerous, powerful, or habit-forming medicines to be used under a health care provider’s supervision can be sold only by prescription. The prescription must be written by a physician, dentist, or advanced practice nurse; otherwise the pharmacist is forbidden to prepare and fill it.

Health care costs are consistently rising. One of the major cost drivers is the world-wide epidemic of diabetes. The estimated total cost of diagnosed diabetes in 2012 is $245 billion, including $176 billion in direct medical cost and $69 billion in reduced productivity. Over 20% percent of health care costs are associated with diabetes care.

SUMMARY

This specification describes technologies relating to health care management.

In general, one innovative aspect of the subject matter described in this specification can be embodied in methods that include the actions of receiving compliance information about a member. The methods include the actions of determining based at least in part on the compliance information that the member is in compliance with the health plan. The methods include the actions of adding the member to a list of compliant members. The methods also include the actions of providing the list of compliant members to at least one third-party.

Other embodiments of this aspect include corresponding computer systems, apparatus, and computer programs recorded on one or more computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

The foregoing and other embodiments can each optionally include one or more of the following features, alone or in combination. Receiving compliance information may include receiving information about an activity undertaken by the member. Providing the list of compliant members to the at least one third party may include determining a method of transmission based on the identity of the third party and transmitting the list to the third party. Providing the list occurs within five seconds of receiving the compliance information. The methods may include the actions of receiving subsequent compliance information about the member, determining based at least in part of the subsequent compliance information that the member is not in compliance with the health plan, removing the member from the list of compliant members, and providing the list of compliant members to at least one third party. The compliance information may be indicative of the members actions with respect to at least one activity based goal. The activities may include at least one of visiting a doctor, getting a lab test, and attending an educational program. The third-party may provide a benefit to the member based on the list. The list may be provided electronically. The methods may include the actions of receiving compliance information about a plurality of members, determining based at least in part on the compliance information whether each of the plurality of members is in compliance with the health plan, adding each compliant member to the list of compliant members, and removing each non-compliant member from the list of compliant members.

Particular embodiments of the subject matter described in this specification can be implemented so as to realize one or more of the following advantages. Patient compliance with a health care plan can be improved. Patients can be provided with rewards in near real time.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 3 illustrates an example of a process for adding and removing members.

Like reference numbers and designations in the various drawings indicate like elements.

DETAILED DESCRIPTION

A system encourages users to improve patient health by providing incentives. Health care costs are consistently rising. One of the major cost drivers is the world-wide epidemic of diabetes. The estimated total cost of diagnosed diabetes in 2012 is $245 billion, including $176 billion in direct medical cost and $69 billion in reduced productivity. Over 20% percent of health care costs are associated with diabetes care.

Patients may be encouraged to adopt good health practice through the use of incentives. Patients may be rewarded for taking action to manage and prevent disease or the complications from disease. One incentive that can be offered is a discount or waiver of cost on prescription medications.

In order for incentives to be effective, they need to be timely. The period of time between taking an action and experiencing the reward should be relatively short. For example, if a system offers discounted or free prescriptions in return for viewing a video or visiting their doctor, the member is more likely to comply if the rewards are enacted shortly after they complete the activity (e.g. within a day, within a half hour, within a few minutes, within a few seconds). Similarly, if the rewards are taken away shortly after the member becomes non-compliant (for example, fails to complete a task within a predetermined time period), the member is more likely to return to compliance.

A system to manage the inventive tracking and benefit allocation may process a large number of items in a short period of time. As such, in order to support the near real time feedback on incentives, computer technology is necessary to receive documents, update records, and distribute information to the various partners of the benefits system. The system described herein can provide a substantial improvement to the performance and effectiveness of incentive based reward programs.

Figure 1:
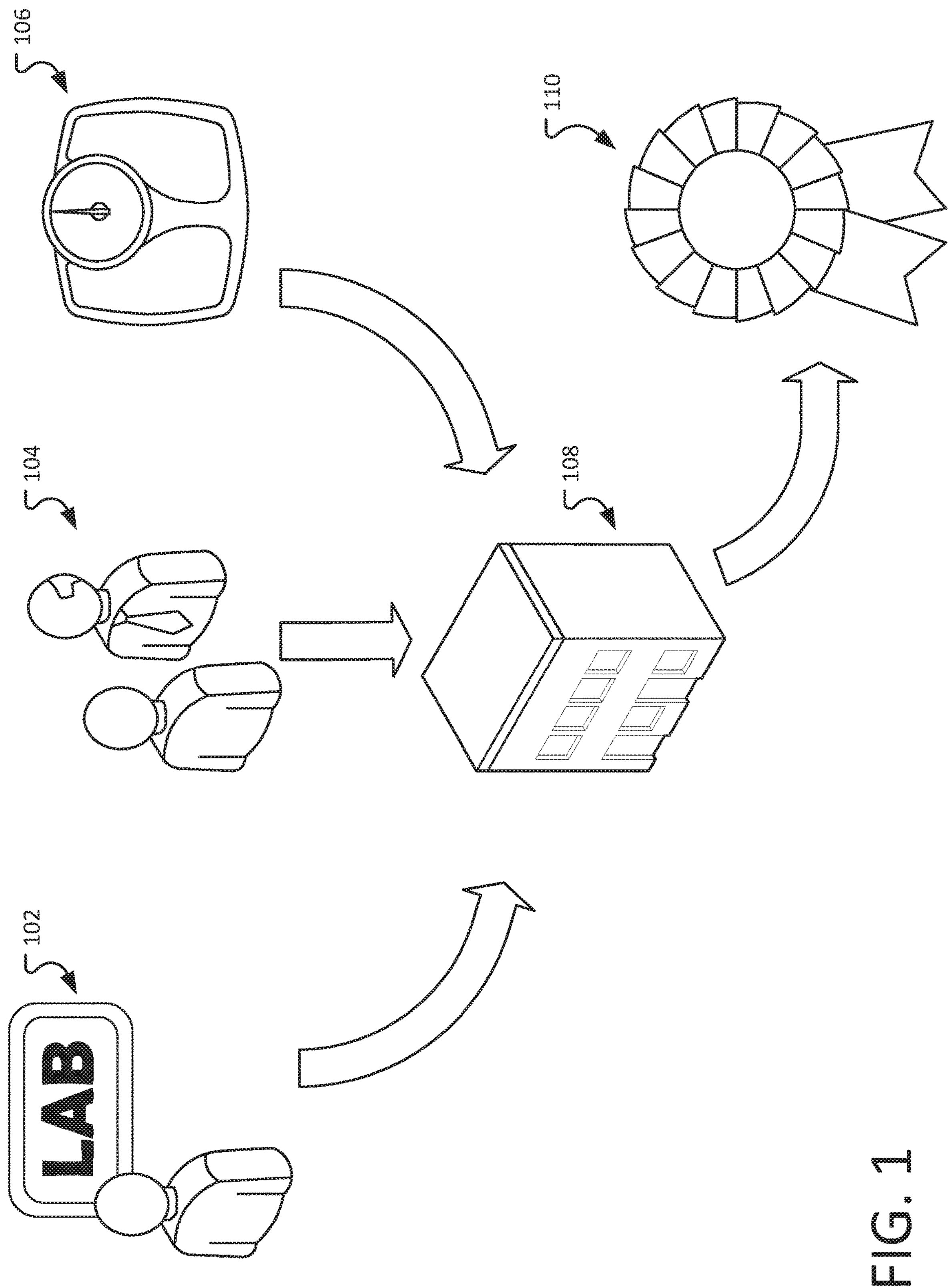
FIG. 1 illustrates an example of providing incentives.

FIG. 1 illustrates an example of providing incentives. A member may be provided with a health plan that acts as a guide to a good health practices and reduce the risks of complications associated with various health issues, such as diabetes or heart disease. For example, the member may be advised to visit a laboratory to have tests run 102 (for example, an A1C test), see their doctor regularly 104, and maintain a healthy weight 106. The health plan may be activity based (for example, visit a lab, visit a doctor, take a course) or may be outcome based (for example, exercise, maintain a predetermined weight, maintain a predetermined blood sugar level, etc.). Results based goals may have predetermined ranges based a target values. For example, weight may be determined based on a desired body mass index (for example, to maintain a normal weight). In some implementations, the health plan may allow for a range of potential values that may deviate from the desired outcome (for example, by 5%, 10%, 15%, 1 standard deviation based on a sample population, etc. . . . ).

Information about a member's compliance with the health plan can be collected by a benefits administrator 108. The benefits administrator 108 can, for example, collect provider confirmation forms and information that show member compliance with the health plan. Member compliance can be encouraged by offering incentives 110 or rewards to compliant members. These incentives can include, for example, a reduction or waiver of out of pocket pharmacy costs. The member may be provided with a benefit card or pharmacy payment discount card to present to a pharmacy in order to redeem the reward.

Figure 2:
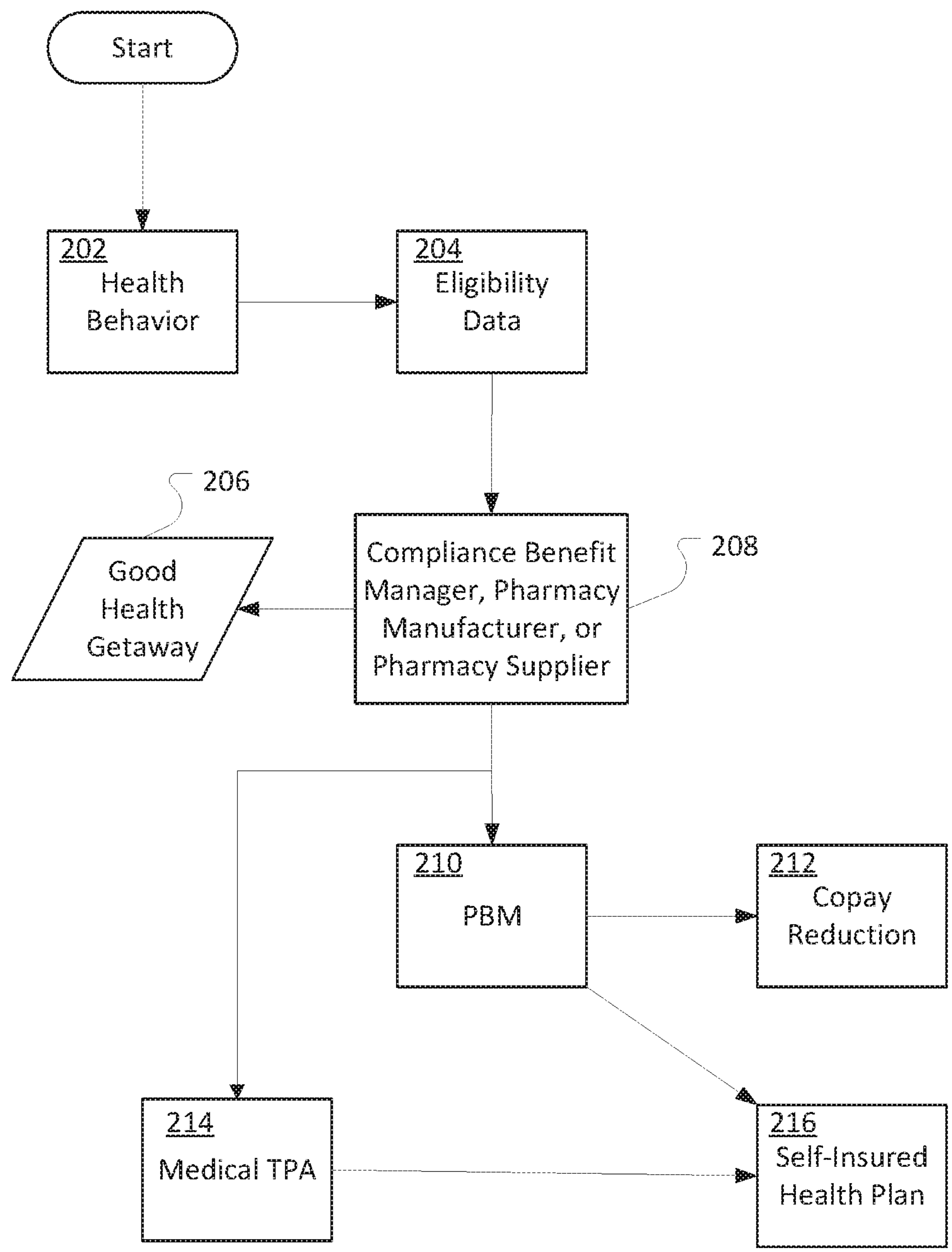
FIG. 2 is a block system diagram for a prescription benefits management system.

Referring to FIG. 2, the provisioning of health plan based incentives may include providing a benefits card than can be activated and deactivated in a timely manner. For example, a benefits card may be activated or deactivated within in near real time (for example, within 5 minutes, 1 minutes, 30 seconds, 10 seconds). The benefits card may be activated or deactivated based on confirmation of the member's completion, re-completion, or lapsing of health plan requirements. The provisioning of the health plan based incentives may be contingent on the member's adherence to defined health behavior(s) according to evidence-based guidelines 202. In general, evidence-based guidelines refers to information that can be verified using extrinsic evidence.

A list of members who are eligible for the incentives, based on their adherence with the health behavior, are listed in eligibility data 204.

The eligibility data 202 can be sent to compliance benefits manager, pharmacy manufacturers, or pharmacy suppliers. In general, a compliance benefits manager is an organization or entity that manages the incentive based benefits program for other prescription benefits managers or medical third party administrators.

A good health gateway 206 is a member portal that displays the compliance data to the member. The good health gateway 206 can be operated, for example, by the compliance benefits manager. A good health gateway may be, for example, a portal or website that enables a member to view information about their incentive based rewards. For example, the member may be able to view actions they need to perform in order to maintain compliance with the program. The member may also be able to view the status of their benefits (for example, if the member is in compliance and therefore currently qualifies for the benefit).

The eligibility data 202 can be sent to the prescription benefits manager 210 and/or a medical third party administrator 214. The prescription benefits manager 210 and/or medical third party administrator 214 may rely on an compliance benefits manager 208 to track and report the compliance of members. The compliance benefits manager 208 may provide a list of eligible members to the prescription benefits manager 210 and/or medical third party administrator 214. The list may be provided electronically, for example, using an application programming interface (API) made available to the compliance benefits manager. In some implementations, each prescription benefits manager 210 and medical third party administrator 214 may provide an API that the compliance benefits manager uses to send information.

The prescription benefits manager enables the pharmacy purchase price paid at the point of sale to include a reduction 212 or elimination of the out-of-pockets costs associated with filling the prescription.

The benefits card allows the qualifying member to access prescription medication supplies at nationwide retail pharmacies 212 and/or through mail order. When a member obtains a prescription medication a pharmacy claim may result. The pharmacy claim can include a request for reimbursement or a point-of-sale reduction or waiver of the member's out of pocket cost at the time of purchase.

The associated pharmacy claim can be adjudicated through 206 a pharmacy supplier, pharmacy manufacturer, or adjunctive pharmacy benefits manager (i.e., a separate manager than the established incumbent pharmacy benefits manager for the member's health plan) by way of an electronically communicated incentive eligibility list 204.

Health behaviors can apply to members of a self-insured employer 216, members of a health plan or to an member.

FIG. 3 illustrates an example of a process for adding and removing members. A compliant member sends 302 a file providing evidence of compliance. Evidence of compliance can be, for example, a lab report showing a lab visit, a record of attendance at a class, information provided by a doctor, etc. . . . . The file can be processed 304. The file can be processed as it is received. For example, a monitoring process can detect that a new file has been received, the monitoring process can trigger the processing of the file.

Each of the received member files are processed 306. If the member is a new member 308, then the member is added to a list of eligible members 326. If the member is a reinstated member, then the list of eligible members 328 is updated with new eligibility dates for the member. In general, a reinstated member is a member that has fallen out of compliance and has subsequently renewed their compliance with the health plan. If the start date and end date for the member new, then the list of eligible members 328 is updated with new eligibility dates for the member.

The process can review the file against the current eligibility list from prescription benefits manager 318. If the member is missing from the current eligibility list from prescription benefits manager then the process terminates the missing member 320. Otherwise, the no change is required 322. For example, a prescription benefits manager or medical third party administrator may maintain a list of eligible members, the process can compare the current list to the list maintained by the prescription benefits manager to identify members who should be removed from the list maintained by the prescription benefits manager or medical third party administrator.

The process can send a daily report 318 including a full list of eligible members with start and end dates populated. In some implementations, the report can be used to verify that systems are correctly synchronized 324. For example, the report can be used to verify that the list of eligible members maintained by the medical third party administrators and/or prescription benefits managers are consistent with the list generated by the process.

Figure 4:
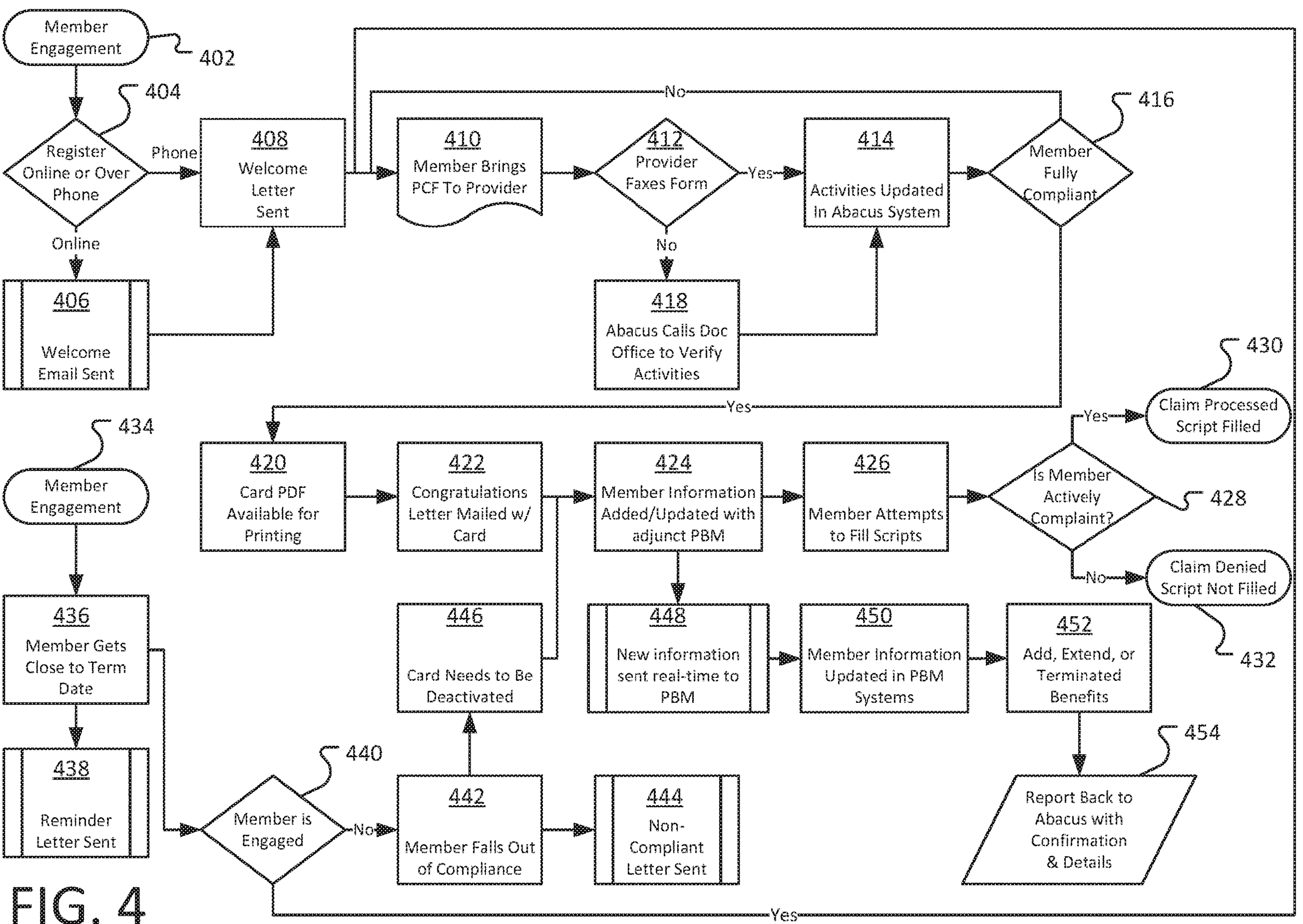
FIG. 4 illustrates an example of a process for managing members.

FIG. 4 illustrates an example of a process for managing members. The process begins with when a member is engaged through the process 402. Member engagement may begin when a new member signs up for the service. For example, the member may be an employee of a company that engages in a contract with a compliance benefit provider. The member may be a member of a health care provider who engages with a compliance benefit provider. Alternatively, the member may have signed up with the compliance benefit provider directly.

The member may register with the service either online, for example, using a form on a website or over the telephone, for example, during a conversation with a customer service representative 404.

If the user's registers online then a welcome e-mail can be sent 406.

A welcome letter may be automatically generated and mailed to the member 408. The welcome letter may include pertinent details about the program, including but not limited to, the requirements to maintain compliance with the health plan and the rewards for being in compliance.

The system can generate a provider confirmation form for the member to bring to their health care provider 410. The provider confirmation form may include questions about the activities of the member, for example, the degree to which the member complies with health plan requirements.

The health care provider fills out the forms provided by the member. The health care provider may transmit the forms to the compliance benefit provider 412. The health care provider may also e-mail or otherwise electronically submit the forms to the compliance benefit provider. In some implementations, the forms may be provided electronically. For example, the health care provider may fill out the form at a website.

If the health care provider does not provide the forms within a pre-determine period of time, for example, 1 week. A customer service representative may call the health care provider to verify the activities of the member 418. In some implementations, the telephone call to verify the activities of the member may be scheduled automatically.

Based on the information provided in the form, or based on information provided during the telephone call with the health care provider, the information about the activities of the member may be updated and stored in a system 414.

Based on the information provided about the activities, the system can determine whether the member is fully compliant 416. If the member is not fully compliant the system can provide a form to the member and request updated/additional information from the health care provider. If the member is fully compliant, the system can make an electronic card available to the member.

An electronic card can be made available to the member 420. The electronic card may be in a format suitable for printing or for presenting using a client device, such as a smart phone, tablet, or similar portable computing device. In some implementations, the electronic card can be a PDF document. In some implementations, the electronic card may be a reward card or other card suitable for storing in a digital wallet. Alternatively, the electronic card may be a bar code or QR code that the member may present to receive benefits.

A congratulations letter can be sent to the member 422. The congratulations letter may inform the member that they have been approved for the program and are currently considered to be in compliance. The congratulations letter may also include a physical card that can be used to obtain benefits associated with the program.

The member's information can be added to a particular system, for example a pharmacy benefits management system 424. Information about the member can be updated on an ongoing basis based on information about on ongoing activities of the member. Updated information can be collected from health care providers, online assessments, and educators.

When a member goes to a pharmacy and attempts to fill a prescription 426, the system checks whether or not the member is listed as actively complaint 428.

If the member is actively complaint then the claim is process and/or the prescription is filled 430. If the member is not actively compliant then the claim is denied and/or the prescription is not filled 432.

Further processing can begin as member engagement 434. As the member approaches their termination date 436, for example, if the contract with the compliance benefit manager has terminated or if the member needs to take action a reminder letter can be sent 438.

The reminder letter is sent to inform the member that they are approaching their term date 438. The reminder letter may include information about how the member can renew his engagement with the compliance benefit manager.

If the member reengages with the compliance benefit manager 440 the system can provide a pdf form for the member to bring to their health care provider.

If the member does not engage with the compliance benefit manager system, then the member is considered non-compliant 442.

A non-compliance letter can be sent 444. The non-compliance letter informs the member that the member is no longer in compliance with the program and the benefits associated with the program will be or have been terminated.

The system determines to deactivate the card 446. The information is updated in the system and the prescription benefits manager is notified as described above.

As new information is made available, it is sent to the pharmacy benefits management system 448. The information can be made available in real-time, subject to the limitations of network latency.

The pharmacy benefits management system updates their records based on the new information provided by the service 450.

The information may cause the pharmacy benefits management system to add a new member to the system 452, extend the existing benefits of the member, or terminate the benefits of the member.

When the pharmacy benefits management system makes updates to a member's status, the pharmacy benefits management system reports the details back to the compliance benefit manager 454.

Figure 5:
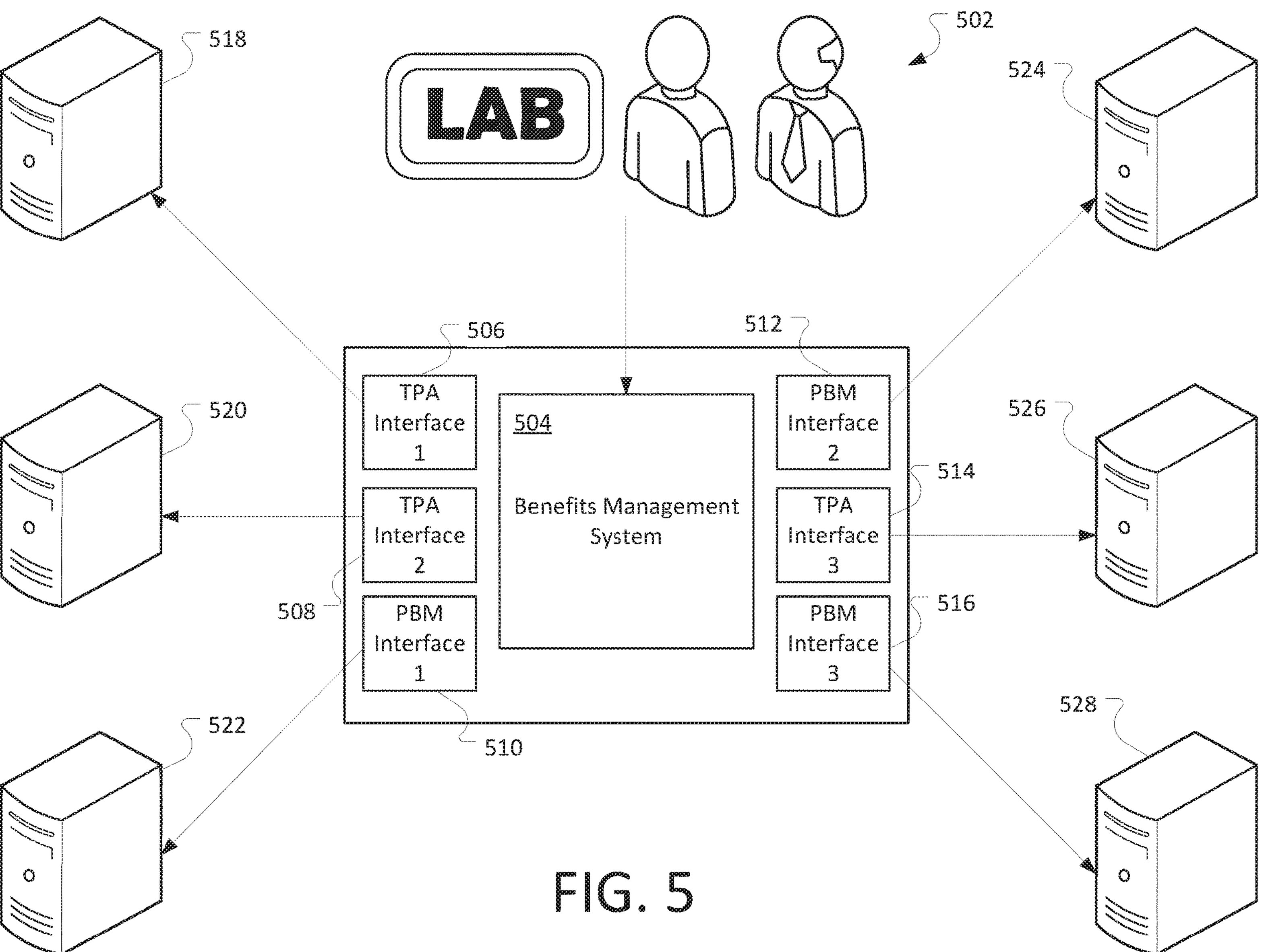
FIG. 5 illustrates an example of a system for managing pharmacy benefits.

FIG. 5 illustrates an example of a system for managing pharmacy benefits. Information is provided by individuals and systems 502, as described above, to a benefits management system 504. The benefits management system 504 may be run, for example, by an compliance benefits manager.

In some scenarios, the benefits management system may process the information provided in a non-readable format. For example, the benefits management system may receive a scanned or faxed document. Processing information in a non-readable format may include, but is not limited to, performing object character recognition, identifying a form (for example, by identifying and reading a bar code or QR code, and analyzing the contents of the document to determine compliance information.

As described above, the benefits management system 504 can generate information about member compliance and can distribute that information to pharmacy benefits managers and medical third party administrators. Communication between the benefits management system and the pharmacy benefits manager and medical third party administrators may occur via secure transmission over a network, for example, the Internet.

In some implementations, the method by which the benefits management system communicates with the pharmacy benefits managers and medical third party administrators may vary from party to party. For example, a medical third party administrator interface 506 may be used to communicate with a medical third party administrator system 518, a medical third party administrator interface 508 may be used to communicate with a medical third party administrator system 520, a pharmacy benefits manager interface 510 may be used to communicate with a pharmacy benefits manager system 522, a pharmacy benefits manager interface 512 may be used to communicate with a pharmacy benefits manager system 524, a medical third party administrator interface 514 may be used to communicate with a medical third party administrator system 526, and a pharmacy benefits manager interface 516 may be used to communicate with a pharmacy benefits manager system 528.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs (i.e., one or more modules of computer program instructions, encoded on computer storage mediums for execution by, or to control the operation of, data processing apparatus). A computer storage medium can be, or be included in, a computer-readable storage device, a computer-readable storage substrate, a random or serial access memory array or device, or a combination of one or more of them. The computer storage medium can also be, or be included in, one or more separate physical components or media (e.g., multiple CDs, disks, or other storage devices). The computer storage medium can be non-transitory.

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example, a programmable processor, to a computer, a system on a chip, or multiple ones, or combinations, of the foregoing The apparatus can include special purpose logic circuitry (e.g., an FPGA (field programmable gate array) or an ASIC (application-specific integrated circuit)). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry (e.g., an FPGA (field programmable gate array) or an ASIC (application-specific integrated circuit)).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive, data from or transfer data to, or both, one or more mass storage devices for storing data (e.g., magnetic, magneto-optical disks, or optical disks), however, a computer need not have such devices. Moreover, a computer can be embedded in another device (e.g., a mobile telephone, a personal digital assistant (PDA), a mobile audio or video player, a game console, a Global Positioning System (GPS) receiver, or a portable storage device (e.g., a universal serial bus (USB) flash drive)), to name just a few. Devices suitable for storing computer program instructions and data include all forms of non-volatile memory, media and memory devices, including by way of example semiconductor memory devices (e.g., EPROM, EEPROM, and flash memory devices), magnetic disks (e.g., internal hard disks or removable disks), magneto-optical disks, and CD-ROM and DVD-ROMdisks. The processor and the memory can be supplemented by, or incorporated in, special purpose logic circuitry.

To provide for interaction with a user, embodiments of the subject matter described in this specification can be implemented on a computer having a display device (e.g., a CRT (cathode ray tube) or LCD (liquid crystal display) monitor)

for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback) and input from the user can be received in any form, including acoustic, speech, or tactile input. In addition, a computer can interact with a user by sending documents to and receiving documents from a device that is used by the user (for example, by sending web pages to a web browser on a user's user device in response to requests received from the web browser). Embodiments of the subject matter described in this specification can be implemented in a computing system that includes a back-end component (e.g., as a data server), a middleware component (e.g., an application server), or a front-end component (e.g., a user computer having a graphical user interface or a Web browser through which a user can interact with an implementation of the subject matter described in this specification), or any combination of one or more such back-end, middleware, or front-end components. The components of the system can be interconnected by any form or medium of digital data communication (e.g., a communication network). Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can, in some cases, be excised from the combination, and the claimed combination may be directed to a sub combination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method comprising:

receiving data representing compliance information from a medical services provider, the compliance information specifying a health care action for a member related to a medical diagnosis of diabetes, the information specifying a date of completion related to the health care action;

wherein the health care action comprises at least one of visiting a doctor, getting a lab test, completing an interview with a healthcare professional, performing a biometric reading through a home-based medical monitoring device or attending an educational program;

determining a health care plan for the member, the health care plan comprising a plurality of additional health care actions for completion within a predetermined timeframe by the member, the additional health care actions being related to the medial diagnosis of diabetes;

determining based at least in part on the compliance information that the member is compliant with the health care plan;

adding the member to a list of compliant members;

within a pre-determined time frame of receiving the compliance information and adding the member to the list of compliant members, sending notification data by a communications network to a client device associated with the member comprising a notification that the member is added to the list of compliant members; and activating, over the communications network in real time or near real time, an electronic card provided to the member by the client device, the electronic card configured to identify, in association with a request for a service by the member with the electronic card, a benefit associated with the service to be provided to the member; and providing data representing the list of compliant members to at least one third-party entity to cause the at least one third-party entity to provide the benefit associated with the service in real time or near real time in response to receiving the request, associated with the activated electronic card, for the service;

maintaining a compliant status for the member in response to receiving compliance data for the member over the communications network;

in response to a failure to receive compliance data for the member over the communications network, determining that the member is no longer compliant with the health care plan;

in response to determining that the member is no longer compliant with the health care plan:

deactivating, over the communications network, in real time or near real time, the electronic card provided to the member; and sending, over the communications network in real time or near real time, a message to the client device of the member specifying that the member is no longer compliant.

2. The computer-implemented method of claim 1, wherein providing the list of compliant members to the at least one third party comprises:

determining a method of transmission based on the identity of the third party; and transmitting the list to the third party.

3. The computer-implemented method of claim 1, wherein providing the list occurs within five seconds of receiving the compliance information.

4. The computer-implemented method of claim 1, further comprising:

receiving subsequent compliance information about the member;

determining based at least in part of the subsequent compliance information that the member is not in compliance with the health plan;

removing the member from the list of compliant members; and providing the list of compliant members to at least one third party.

5. The computer-implemented method of claim 1, wherein the service discount comprises a co-pay reduction.

6. The computer-implemented method of claim 1, wherein the list is provided electronically.

7. The computer-implemented method of claim 1, further comprising:

receiving compliance information about a plurality of members;

determining based at least in part on the compliance information whether each of the plurality of members is in compliance with the health plan;

adding each compliant member to the list of compliant members; and removing each non-compliant member from the list of compliant members.

8. A non-transitory computer storage medium encoded with computer program instructions that when executed by one or more computers cause the one or more computers to perform operations comprising:

receiving compliance information from a medical services provider, the compliance information specifying a health care action for a member related to a medical diagnosis of diabetes, the information specifying a date of completion related to the health care action;

wherein the health care action comprises at least one of visiting a doctor, getting a lab test, completing an interview with a healthcare professional, performing a biometric reading through a home-based medical monitoring device or attending an educational program;

determining a health care plan for the member, the health care plan comprising a plurality of additional health care actions for completion within a predetermined timeframe by the member, the additional health care actions being related to the medial diagnosis of diabetes;

determining based at least in part on the compliance information that the member is compliant with the health care plan;

adding the member to a list of compliant members;

within a pre-determined time frame of receiving the compliance information and adding the member to the list of compliant members, sending notification data by a communications network to a client device associated with the member comprising a notification that the member is added to the list of compliant members;

activating, over the communications network in real time or near real time, an electronic card provided to the member by the client device, the electronic card configured to identify, in association with a request for a service by the member with the electronic card, a benefit associated with the service to be provided to the member; and providing data representing the list of compliant members to at least one third-party entity to cause the at least one third-party entity to provide the benefit associated with the service in real time or near real time in response to receiving the request, associated with the activated electronic card, for the service;

maintaining a compliant status for the member in response to receiving compliance data for the member over the communications network;

in response to a failure to receive compliance data for the member over the communications network, determining that the member is no longer compliant with the health care plan; and in response to determining that the member is no longer compliant with the health care plan:

deactivating, over the communications network, in real time or near real time, the electronic card provided to the member; and sending, over the communications network in real time or near real time, a message to the client device of the member specifying that the member is no longer compliant.

9. The non-transitory computer storage medium of claim 8, wherein providing the list of compliant members to the at least one third party comprises:

determining a non-transitory computer storage medium of transmission based on the identity of the third party; and transmitting the list to the third party.

10. The non-transitory computer storage medium of claim 8, wherein providing the list occurs within five seconds of receiving the compliance information.

11. The non-transitory computer storage medium of claim 8, further comprising:

receiving subsequent compliance information about the member;

determining based at least in part of the subsequent compliance information that the member is not in compliance with the health plan;

removing the member from the list of compliant members; and providing the list of compliant members to at least one third party.

12. The non-transitory computer storage medium of claim 8, wherein the third-party provides a benefit to the member based on the list.

13. The non-transitory computer storage medium of claim 8, wherein the list is provided electronically.

14. A system comprising:

one or more computers and one or more storage devices storing instructions that are operable, when executed by the one or more computers, to cause the one or more computers to perform operations comprising:

receiving data representing compliance information from a medical services provider, the compliance information specifying a health care action for a member related to a medical diagnosis of diabetes, the information specifying a date of completion related to the health care action;

wherein the health care action comprises at least one of visiting a doctor, getting a lab test, completing an interview with a healthcare professional, performing a biometric reading through a home-based medical monitoring device or attending an educational program;

determining a health care plan for the member, the health care plan comprising a plurality of additional health care actions for completion within a predetermined timeframe by the member, the additional health care actions being related to the medial diagnosis of diabetes;

determining based at least in part on the compliance information that the member is compliant with the health care plan;

adding the member to a list of compliant members;

within a pre-determined time frame of receiving the compliance information and adding the member to the list of compliant members, sending notification data by a communications network to a client device associated with the member comprising a notification that the member is added to the list of compliant members;

activating, over the communications network in real time or near real time, an electronic card provided to the member by the client device, the electronic card configured to identify, in association with a request for a service by the member with the electronic card, a benefit associated with the service to be provided to the member; and providing data representing the list of compliant members to at least one third-party entity to cause the at least one third-party entity to provide the benefit associated with the service in real time or near real time in response to receiving the request, associated with the activated electronic card, for the service;

maintaining a compliant status for the member in response to receiving compliance data for the member over the communications network;

in response to a failure to receive compliance data for the member over the communications network, determining that the member is no longer compliant with the health care plan; and in response to determining that the member is no longer compliant with the health care plan:

deactivating, over the communications network, in real time or near real time, the electronic card provided to the member; and sending, over the communications network in real time or near real time, a message to the client device of the member specifying that the member is no longer compliant.

15. The computer-implemented method of claim 1, wherein the compliance information is verified in response to a transaction associated with an electronic card, and wherein the service discount is provided in relation to the transaction associated with the electronic card.

16. A computer-implemented method comprising:

receiving data representing compliance information about a member for a health plan, the compliance information being verified in association with a transaction that is executed with an electronic card specifying the member, the electronic card configured to identify, in association with a request for a service by the member with the electronic card, a benefit associated with the service to be provided to the member;

determining based at least in part on the compliance information that the member is in compliance with the health plan;

adding the member to a list of compliant members;

providing the list of compliant members to at least one third-party; and within a pre-determined time frame of receiving the compliance information and adding the member to the list of compliant members, sending notification data by a communications network to a client device associated with the member comprising a notification that the member is added to the list of compliant members;

activating, over the communications network in real time or near real time, an electronic card provided to the member by the client device;

providing data representing the list of compliant members to at least one third-party entity to cause the at least one third-party entity to provide the benefit associated with the service in real time or near real time in response to receiving the request, associated with the activated electronic card, for the service;

maintaining a compliant status for the member in response to receiving compliance data for the member over the communications network; and in response to a failure to receive compliance data for the member over the communications network, determining that the member is no longer compliant with the health care plan;

in response to determining that the member is no longer compliant with the health care plan:

deactivating, over the communications network, in real time or near real time, the electronic card provided to the member; and sending, over the communications network in real time or near real time, a message to the client device of the member specifying that the member is no longer compliant.

* * * * *